United States Patent
Quinn-Gorham et al.

(10) Patent No.: US 11,013,529 B2
(45) Date of Patent: May 25, 2021

(54) MULTIPLE BLADE HANDLE SYSTEM

(71) Applicant: TUSKEGEE UNIVERSITY, Tuskegee, AL (US)

(72) Inventors: Deidre Quinn-Gorham, Tuskegee, AL (US); Sharanabasaweshwara Asundi, Tuskegee, AL (US); Jimesh Bhagatji, Tuskegee, AL (US)

(73) Assignee: Tuskegee University, Tuskegee, AL (US)

( * ) Notice: Subject to any disclaimer, the term of this patent is extended or adjusted under 35 U.S.C. 154(b) by 0 days.

(21) Appl. No.: 16/515,591

(22) Filed: Jul. 18, 2019

(65) Prior Publication Data

US 2020/0022721 A1    Jan. 23, 2020

Related U.S. Application Data

(60) Provisional application No. 62/700,693, filed on Jul. 19, 2018.

(51) Int. Cl.
*A61B 17/3213* (2006.01)
*A61B 17/3211* (2006.01)

(52) U.S. Cl.
CPC . *A61B 17/3213* (2013.01); *A61B 2017/32113* (2013.01)

(58) Field of Classification Search
CPC .................. A61B 17/3213; A61B 2017/32113
USPC .......................................... 30/152, 155, 156
See application file for complete search history.

(56) References Cited

U.S. PATENT DOCUMENTS

| | | | | |
|---|---|---|---|---|
| 4,498,236 A * | 2/1985 | McIntyre | ................ | B26B 21/24 30/34.1 |
| 4,587,730 A * | 5/1986 | Iten | ..................... | B26B 21/4037 30/32 |
| 5,230,152 A * | 7/1993 | Kennedy | ................. | B26B 5/001 30/162 |
| 5,571,127 A * | 11/1996 | DeCampli | .......... | A61B 17/3211 30/125 |
| 6,928,738 B2 * | 8/2005 | Segrea | .................... | B26B 21/40 30/34.1 |
| 7,774,941 B2 * | 8/2010 | Johnson | ................ | B26B 11/008 30/162 |
| 2014/0366387 A1 * | 12/2014 | Schuft | ..................... | B26B 5/001 30/293 |

(Continued)

OTHER PUBLICATIONS

Double Handle Scapel, https://www.sklarcorp.com/scalpels/scalpel-handle-20716.

*Primary Examiner* — Hwei-Siu C Payer
(74) *Attorney, Agent, or Firm* — Beusse Sanks, PLLC

(57) ABSTRACT

A handle system includes a body extending between a first end and a second end. The handle system also includes a slot extending, at least partially, in the body, the slot forming a cavity. The handle system further includes a carrier arranged, at least partially, within the slot, the carrier further comprising a friction locker and at least one arm coupled to the friction locker, the at least one arm being rotatable about the friction locker. The handle system also includes a cap arranged on at least one of the first end or the second end. The handle system further includes a blade coupled to the at least one arm, the blade being rotatable about the axis between a retracted position where the blade is positioned within the slot and an extended position where the blade extends outwardly from the body.

15 Claims, 6 Drawing Sheets

(56) References Cited

U.S. PATENT DOCUMENTS

2017/0071619 A1\* 3/2017 Arrigo ............... A61B 17/3211
2017/0151682 A1\* 6/2017 Cheng ....................... B26B 5/00
2018/0250836 A1\* 9/2018 Hinderer ................... B26B 1/06
2020/0022721 A1\* 1/2020 Quinn-Gorham ...........................
A61B 17/3213

\* cited by examiner

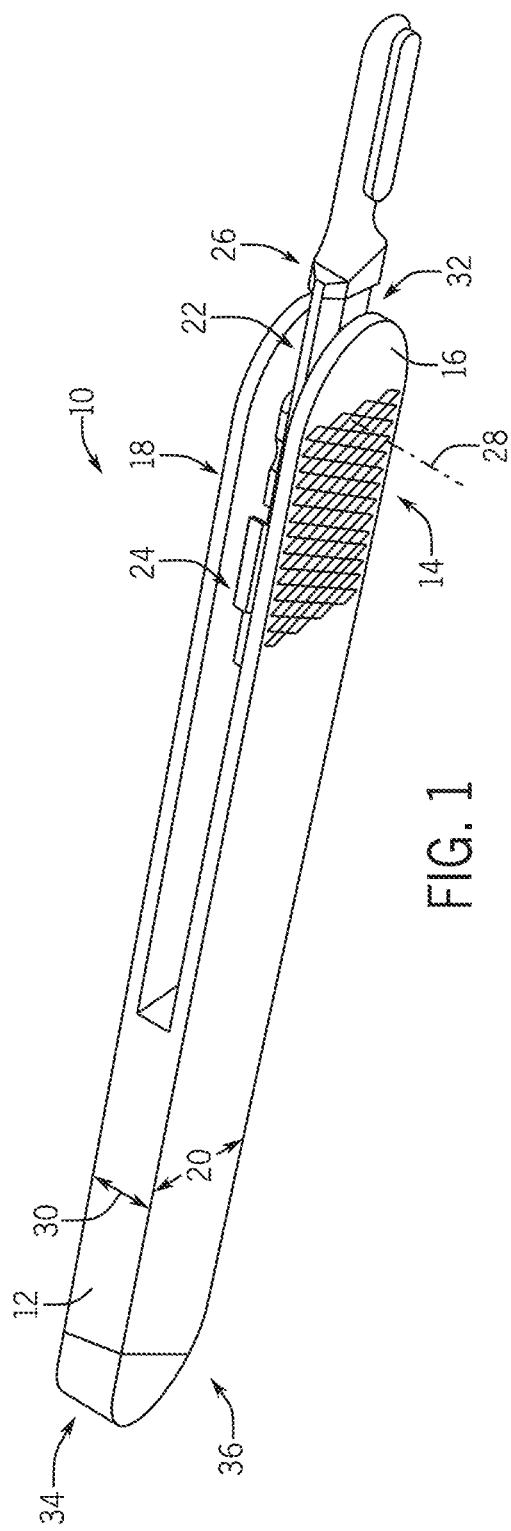
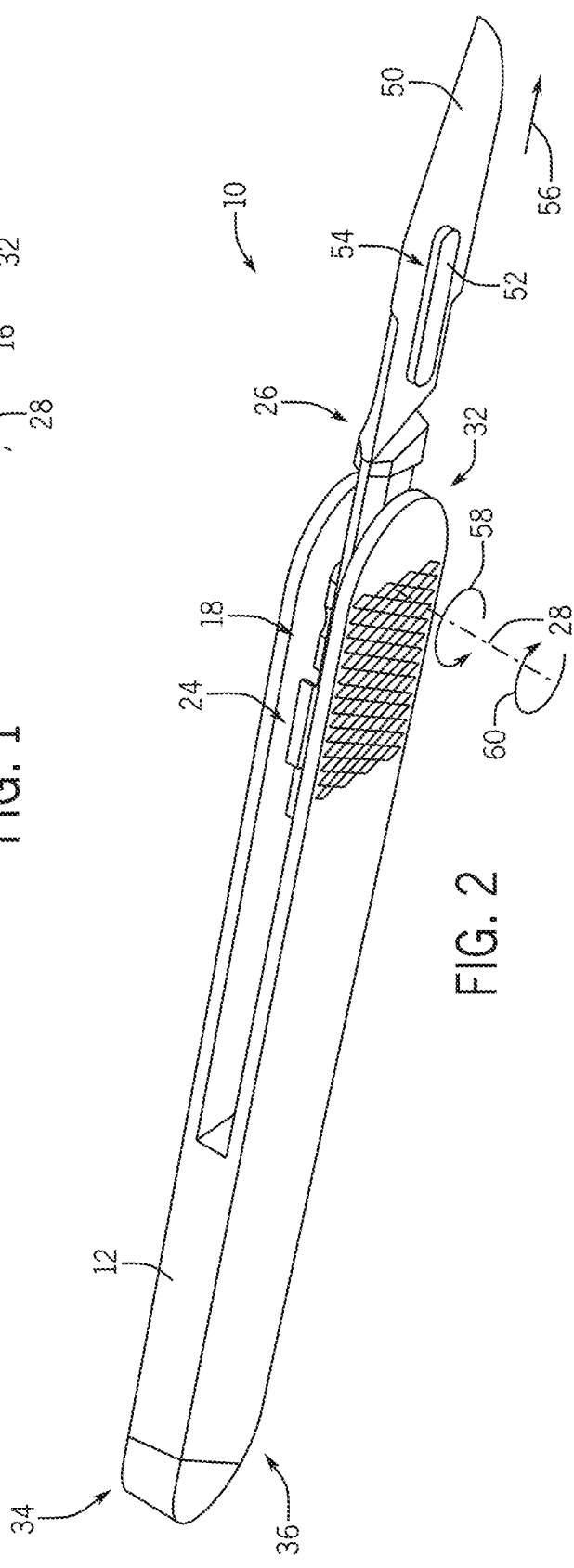
FIG. 1
FIG. 2

MULTIPLE BLADE HANDLE SYSTEM

CROSS-REFERENCE TO RELATED APPLICATIONS

This application claims priority to U.S. Provisional Patent Application No. 62/700,693, filed Jul. 19, 2018 titled "MULTIPLE BLADE HANDLE SYSTEM," the full disclosure of which is incorporated herein by reference it is entirety.

BACKGROUND

Field of the Invention

The present disclosure relates to handle systems for deploying cutting tools. More particularly, the present disclosure relates to systems and methods for mounting multiple cutting tools, such as scalpel blades, onto a single handle.

Description of Related Art

During surgical operations, doctors may utilize a variety of different cutting tools (e.g., scalpel blades, blades) throughout a procedure. These blades may differ in size, and as a result, be mounted on different handles to provide proper leverage or the like during use. The large variety of handles and blades may be challenging to properly change during surgery, for example, as at least one person of the surgical team will be drawn away from the patient in order to change out the scalpel blades. Furthermore, changing blades during surgery incorporates an inherent risk that the blades may cut or otherwise contact sterile surfaces. Moreover, the variety may be difficult to transport and use in rural settings, where full hospital facilities may be unavailable.

SUMMARY

Applicants recognized the problems noted above herein and conceived and developed systems and methods for a handle system that may carry and deploy a variety of scalpel blades using a single handle.

In certain embodiments, a handle system includes a body extending between a first end and a second end. The handle system also includes a slot extending, at least partially, in the body, the slot forming a cavity. The handle system further includes a carrier arranged, at least partially, within the slot, the carrier further comprising a friction locker and at least one arm coupled to the friction locker, the at least one arm being rotatable about the friction locker. The handle system also includes a cap arranged on at least one of the first end or the second end. The handle system further includes a blade coupled to the at least one arm, the blade being rotatable about the axis between a retracted position where the blade is positioned within the slot and an extended position where the blade extends outwardly from the body.

In certain embodiments, a handle system includes a body, a cavity formed within the body, and a carrier, having at least one arm, arranged within the cavity, the at least one arm being rotatable about an axis of the carrier. The handle system also includes a rotation limiter positioned proximate the at least one arm and arranged within the cavity, the rotation limiter blocking rotation of the arm beyond a predetermined position. The handle system further includes a blade coupled to the at least one arm.

In certain embodiments, a method for using a handle system includes rotating a first blade, coupled to an arm, about an axis in a first direction to transition the first blade out of a cavity in a body of the handle system. The method also includes rotating the first blade in a second direction, opposite the first direction, to transition the first blade into the body. The method further includes rotating a second blade, coupled to a second arm, about the axis in the first direction to transition the second blade out of the cavity.

BRIEF DESCRIPTION OF DRAWINGS

Various embodiments in accordance with the present disclosure will be described with reference to the drawings, in which:

FIG. 1 is an isometric view of an embodiment of a handle, in accordance with embodiments of the present disclosure;

FIG. 2 is an isometric view of an embodiment of a handle system including a blade, in accordance with embodiments of the present disclosure;

DETAILED DESCRIPTION

Figure 3:
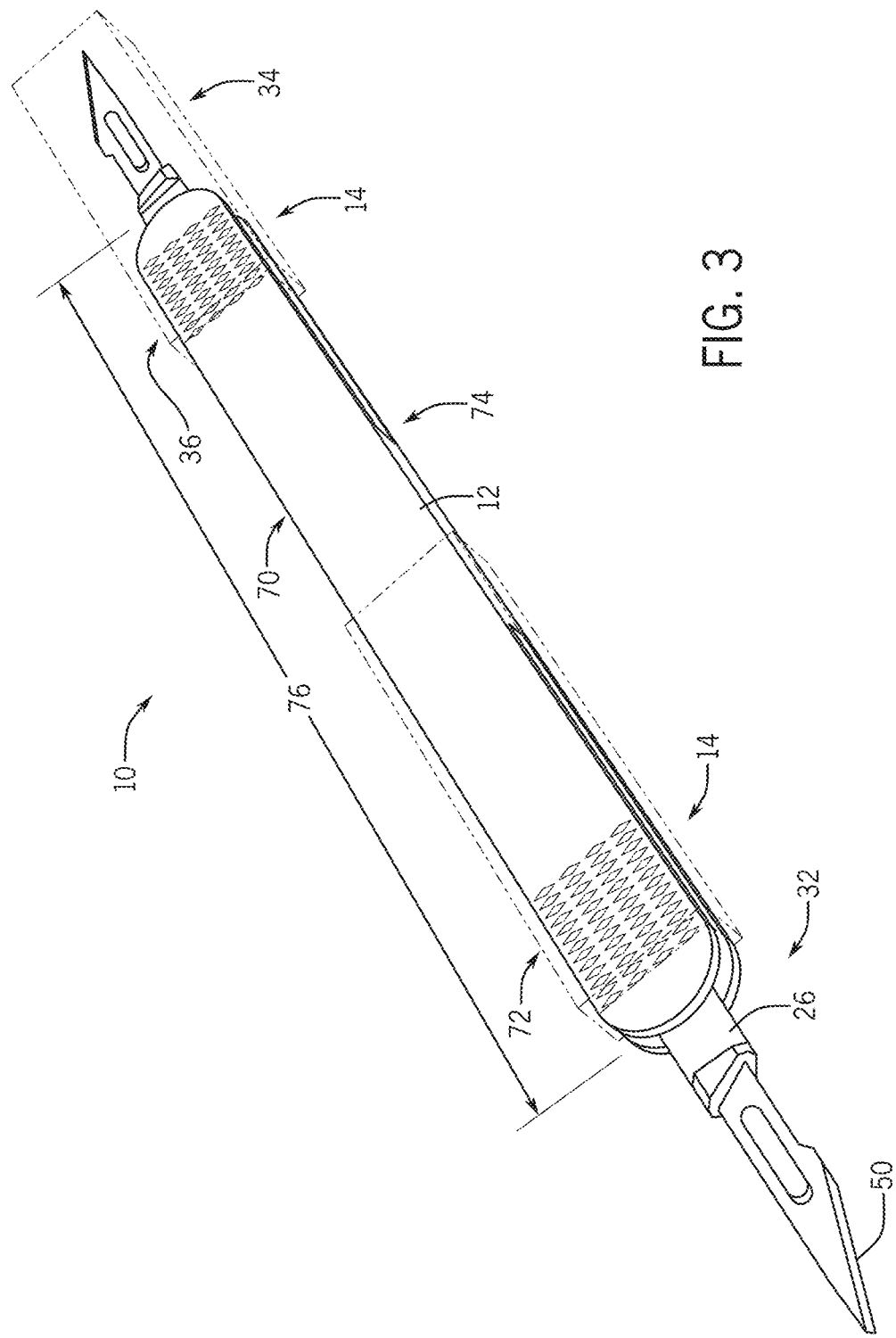
FIG. 3 is an isometric view of an embodiment of a handle system illustrating a pair of blades mounted about a common axis, in accordance with embodiments of the present disclosure.

The foregoing aspects, features, and advantages of the present disclosure will be further appreciated when considered with reference to the following description of embodiments and accompanying drawings. In describing the embodiments of the disclosure illustrated in the appended drawings, specific terminology will be used for the sake of clarity. However, the disclosure is not intended to be limited to the specific terms used, and it is to be understood that each specific term includes equivalents that operate in a similar manner to accomplish a similar purpose.

When introducing elements of various embodiments of the present disclosure, the articles "a", "an", "the", and "said" are intended to mean that there are one or more of the elements. The terms "comprising", "including", and "having" are intended to be inclusive and mean that there may be additional elements other than the listed elements. Any examples of operating parameters and/or environmental conditions are not exclusive of other parameters/conditions of the disclosed embodiments. Additionally, it should be understood that references to "one embodiment", "an embodiment", "certain embodiments", or "other embodiments" of the present disclosure are not intended to be interpreted as excluding the existence of additional embodiments that also incorporate the recited features. Furthermore, reference to terms such as "above", "below", "upper", "lower", "side", "front", "back", or other terms regarding orientation or direction are made with reference to the illustrated embodiments and are not intended to be limiting or exclude other orientations or directions.

Embodiments of the present disclosure include a handle system for storing and deploying a plurality of blades. The blades may be coupled to a carrier including arms that are rotatably mounted to a friction locker. The friction locker may enable rotation of the arms about an axis to transition the arms, and therefore the blades, from a retracted position (e.g., shrouded position, enclosed position, shielded position, closed position, swiveled in position, etc.) where the blades are shrouded by a body of the handle to an extended position (e.g., exposed position, outward position, working position, open position, swiveled out position, etc.) where the blades extend outwardly and away from the body. In various embodiments, the blades may be different sizes, thereby improving the functionality of the handle system compared to traditional scalpels that include a single blade on a single handle. The body may include an extendable portion that enables adjustment of a length of the body. Accordingly, systems and methods of the present disclosure describe a handle system that enables storage and use of multiple blades using the same handle, which may be advantageous in rural environments where carrying multiple handles and blades may be difficult, and where changing blades and/or handles during surgical procedures may be undesirable.

FIG. 1 is an isometric view of an embodiment of a handle system 10 that includes a body 12, which may be utilized by a healthcare professional to hold the handle system 10, for example, during surgical procedures. The illustrated body 10 includes a textured region 14 on an outer surface 16, which may include knurling or the like to improve the grip upon the body 12. It should be appreciated that while the illustrated textured region 14 is only over a portion of the body 12, that the textured region 14 may extend over a larger region and also be present on the back side of the body 12, which is not visible in the embodiment illustrated in FIG. 1. The body 12 of the embodiment illustrated in FIG. 1 further includes a slot 18, which may extend through the height 20 of the body 12, in certain embodiments. The slot 18, as will be described in detail below, forms, at least in part, a cavity 22 for holding one or more cutting tools, which may be referred to as blades. The slot 18 further includes a rotation limiter 24 and receives a carrier 26. As will be described in detail below, the carrier 26 may be configured to rotate about an axis 28 extending through the body 12 in a direction generally perpendicular to a width 30 of the body 12. The rotation limiter 24 may be utilized to limit rotation of the carrier 26, or at least a portion thereof, within a predetermined range. In various embodiments, the range may be approximately 180 degrees.

In various embodiments, the slot 18 is at a first end 32 of the body 12 and a cap 34 is arranged at a second end 36, opposite the first end 32. The cap 34 may cover a second slot, in various embodiments. That is, as will be described below, the handle system 10 may include slots, carriers, and blades at both ends, thereby increasing a total number of different blades that may be carried and used with a single handle system 10.

FIG. 2 is an isometric view of an embodiment of the handle system 10 in which a blade 50 extends outwardly from the body 12 while arranged on the carrier 26. In various embodiments, the carrier 26 includes a tongue 52 that mates with a groove or aperture 54 in the blade 50, thereby coupling the blade 50 to the carrier 26. As described above, the carrier 26 may rotate, at least in part, about the axis 28 to transition the blade 50 from a position within the slot 18 to a position outside the slot 18 and extending in a first direction 56 away from the body 12. It should be appreciated that, while in the slot 18, the blade 50 is shrouded to reduce the likelihood a person holding the body 12 of the handle system 10 may be cut or otherwise interact with the blade 50. The illustrated rotation limiter 24 blocks continued rotation of the carrier 26 in a first rotational direction 58 to thereby secure the blade 50 in position, for example during an operation where a steady position of the blade 50 may be desirable. In the illustrated embodiment, the movement in the first rotational direction 58 rotationally translates the position of the blade 50 such that a bottom portion of the blade 50 (e.g., a cutting portion) may be arranged to face substantially upward (e.g., such that the cutting portion is pointed in a direction toward an opening of the slot 18 and closer to an opening of the slot 18) while retracted within the body 12. In various embodiments, a lock or other feature may be incorporated to maintain the blade 50 in the illustrated extended position. Thereafter, the blade 50 may be rotated about the axis 28 in a second rotational direction 60, opposite the first rotational direction 58, to return the blade 50 to the extended position shown in FIG. 2. Similarly, in various embodiments, movement in the second rotational direction 60 rotationally translates the position of the blade 50 such that a bottom portion of the blade 50 (e.g., a cutting portion) may be arranged to face substantially upward (e.g., substantially perpendicular to the direction 56 such that the cutting portion is pointed in a direction away from an opening of the slot 18 and further from an opening of the slot 18) while retracted within the body 12. While not visible in FIG. 2, in various embodiments the carrier 26 may include a second blade attached to an opposite end thereof. The blades may be independently rotatable, in various embodiments.

FIG. 3 is a schematic isometric view of an embodiment of the handle system 10 wherein the body 12 includes an extendable portion 70. In the illustrated embodiment, the blade 50 extends out of the body 12 in the extended position, for example via rotation about the axis 28 (FIG. 2). Further illustrated is the textured region 14 on both the first end 32 and the second end 36, which may be partially obscured by the cap 34. It should be appreciated that the textured region 14 may, at least partially, facilitate coupling of the cap 34 to the body 12.

Figure 4:
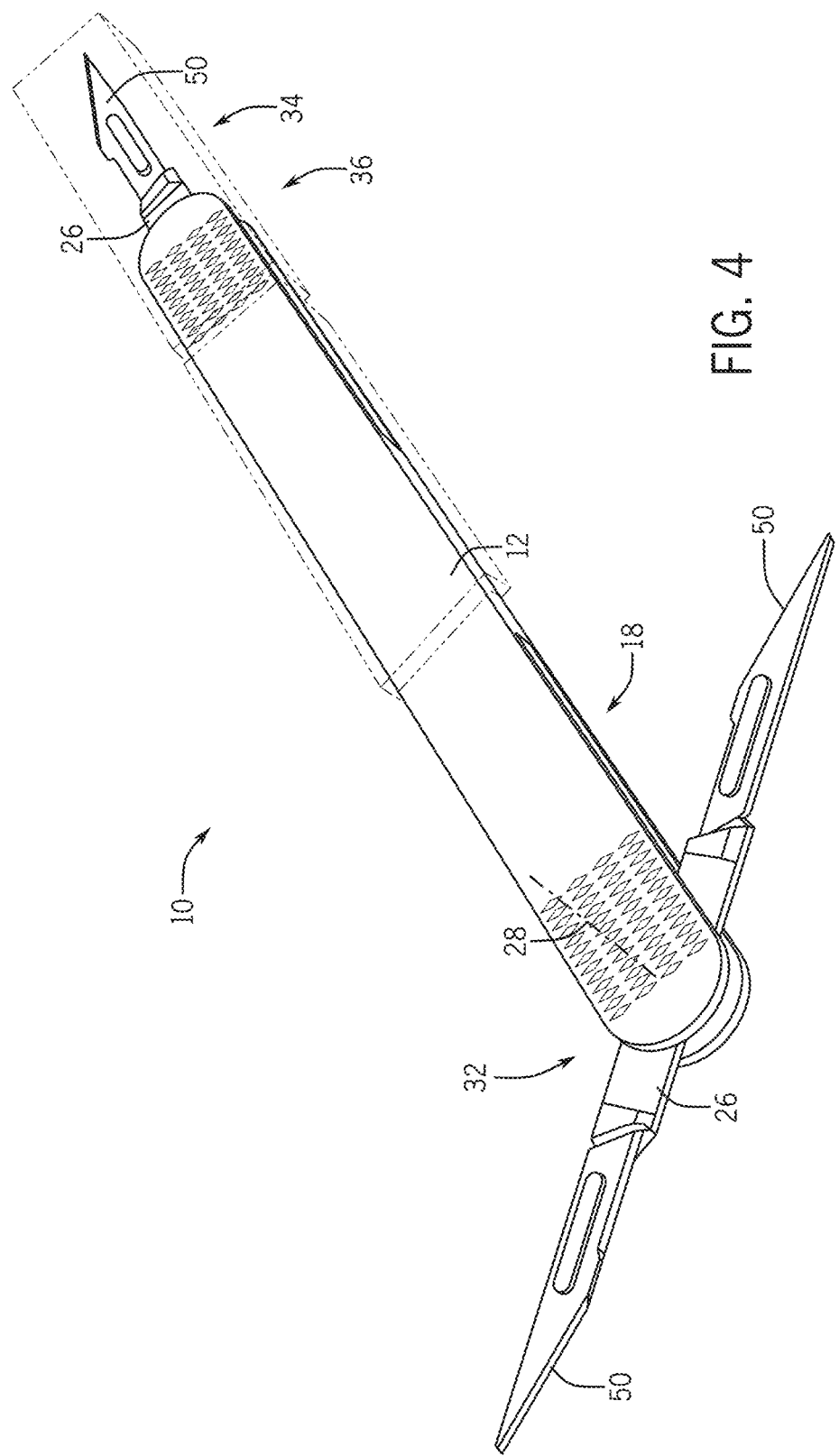
FIG. 4 is an isometric view of an embodiment of a handle system, in accordance with embodiments of the present disclosure.

In the illustrated embodiment, the extendable portion 70 is illustrated between a first body portion 72 and the cap 34. Additionally, portions of the body 12 are illustrated in phantom lines to facilitate the present discussion to illustrate how the body 12 appeared prior to activation of the extendable portion 70. As shown, a first body portion 72 may couple to the cap 34 (by moving the first body portion 72 to overlap the extendable portion 70), as shown in FIG. 4, thereby obscuring the extendable portion 70, in various embodiments. However, it may be advantageous to have a longer body 12, for example, if the operator has larger hands and it is more comfortable to use the larger handle. Accordingly, in various embodiments, a sliding mechanism 74, such as a tongue and groove arrangement or a telescoping mechanism, may be utilized to facilitate extension of the body 12 such that the extendable portion 70 is arranged between the first body portion 72 and the cap 34. Accordingly, a length 76 of the body 12 may be adjusted, depending on whether the extendable portion 70 is utilized. It should be appreciated that, in various embodiments, the extendable portion 70 may be partially utilized, for example, by including stops or tension elements along the sliding mechanism 74 to enable adjustment of the length 76 over a range of different values.

FIG. 4 is an isometric view of an embodiment of the handle system 10 illustrating an embodiment where blades 50 of a pair of blades are independently rotated outside of the slot 18. It should be appreciated that, in use, one blade 50 of the pair of blades 50 may be in the extended position while the other blade 50 of the pair of blades 50 may be retracted within the body 12. Accordingly, the embodiment illustrated in FIG. 4 is for illustrative purposes to demonstrate that, in various embodiments, the blades 50 are independently rotatable about the axis 28. As will be described below, in various embodiments a friction locker may be utilized to facilitate rotation between the retracted and extended positions. In the illustrated embodiments, the blades 50 are different sizes. Accordingly, the handle system 10 provides improved functionality over a traditional scalpel, which only includes a single blade on a single handle. As a result, if used in a rural environment, the illustrated handle system 10 will reduce the amount of equipment transported. In various embodiments, the handle system 10 may also be constructed from a disposable material, such as a plastic, and as a result, may be thrown away after use, which may be more sanitary and safer than subsequent cleaning efforts.

As noted above, FIG. 4 also illustrates, in phantom lines, the cap 34 and the first body portion 72 in a position prior to activation of the extendable portion 70.

Figure 5:
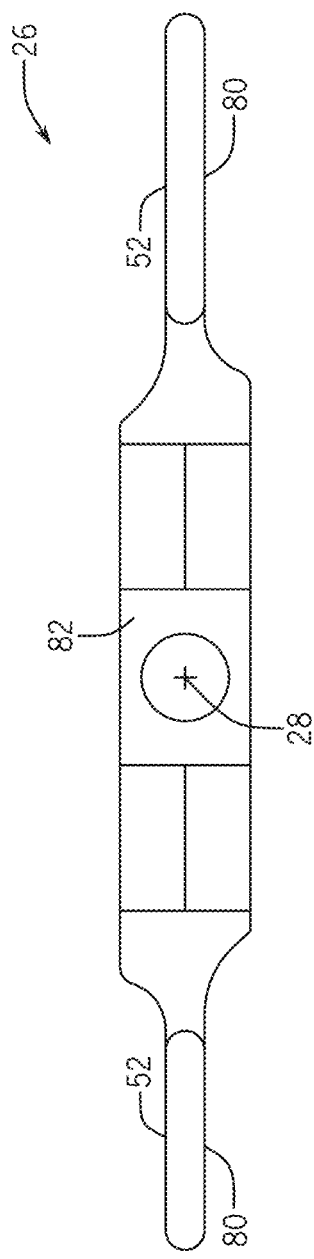
FIG. 5 is a schematic top plan view of an embodiment of a blade holder, in accordance with embodiments of the present disclosure.

FIG. 5 is a top plan view of an embodiment of the carrier 26. The illustrated carrier 26 may accommodate two different blades 50, however it should be appreciated that the carrier 26 may be designed to accommodate 1 blade, 3 blades, 4 blades, 5 blades, or any reasonable number of blades. The illustrated carrier 26 includes arms 80 that are coupled to a friction locker 82. It should be appreciated that the friction locker 82 may also be referred to as a slip joint. The friction locker 82 may include a spring bar that holds the blade in the retracted position. As the force of the spring is overcome, the blade 50, via the arm 80, may rotate about the axis 28 until the rotation limiter 24 (not shown) interacts with the arm 80 and/or the blade 50.

In various embodiments, the arms 80 are independently rotatable relative to one another. In other embodiments, the arms 80 may be fixed to rotate at the same time about the axis 28. As shown in FIG. 5, the arms 80 include the tongue 52 for coupling to the aperture of the blade 50. In the illustrated embodiment, the tongues 52 are different sizes, which may be utilized to accommodate blades 50 having different sized apertures and/or different sized blades.

Figure 6:
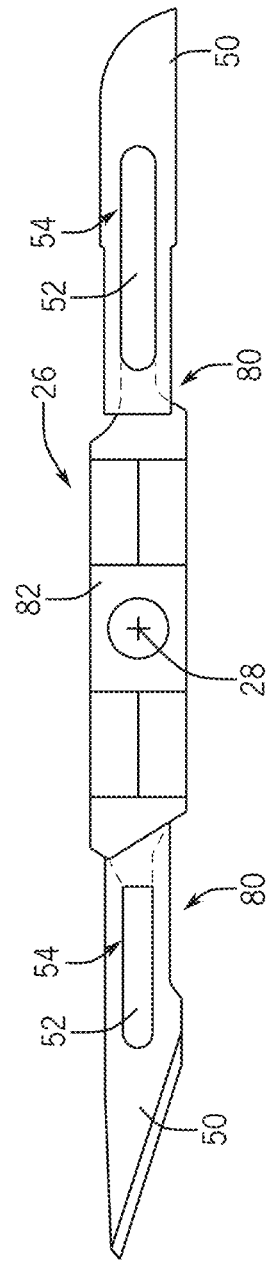
FIG. 6 is a schematic top plan view of an embodiment of a blade holder and a pair of blades, in accordance with embodiments of the present disclosure.

FIG. 6 is a top plan view of an embodiment of the carrier 26 including blades 50 on the arms 80. The respective blades 50 are attached to the different arms 80 via the tongues 52 and the apertures 54. As illustrated, the blades 50 have different shapes and different sizes. For example, the blades 50 may have different cutting surface lengths or widths. Moreover, the illustrated blades 50 include a substantially straight edge and an angled edge. As a result, the functionality of the handle system 10 is improved over a traditional single blade scalpel or a set of scalpels that is frequently changed out during operations. Not shown are caps 34 that can be used to cover the blade not currently in use by the operator.

Figure 7:
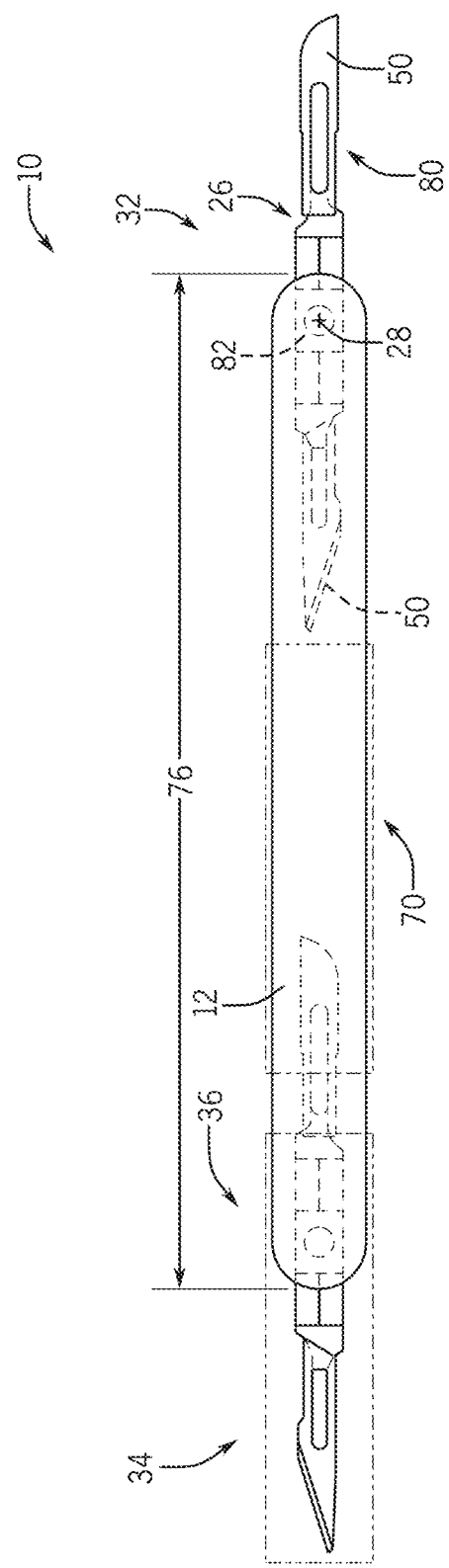
FIG. 7 is a schematic top plan view of an embodiment of a handle system in an extended position, in accordance with embodiments of the present disclosure.

FIG. 7 is a schematic top plan view of an embodiment of the handle system 10 including a pair of blades 50 arranged at both the first end 32 and the second end 36. In the illustrated embodiment, the blade 50 extends in the first direction 56 (FIG. 2) from the first end 32 while the cap 34 is arranged at the second end 36, which covers the blades at the second end 36. The illustrated handle system 10 includes the extendable portion 70, which enables adjustment of the length 76 of the body 12. As shown, the axis 28 extends substantially through the friction locker 82, thereby providing a pivot for rotation of the arms 80 to transition the blades 50 between the extended position and the retracted position. It should be appreciated that while the illustrated embodiment includes 4 blades 50 as part of the handle system 10, in other embodiments a different number of blades 50 may be included. For example, in various embodiments, there may be 1, 2, 3, 4, 5, 6, 7, 8, 9, 10, or any reasonable number of blades 50. Furthermore, the blades 50 may vary in size and shape. In this manner, the handle system 10 may provide a greater variety of blades 50 in a compact package to facilitate working in remote areas or to reduce the time and effort utilized to change out blades on scalpel handles that accommodate only a single blade.

Figure 8:
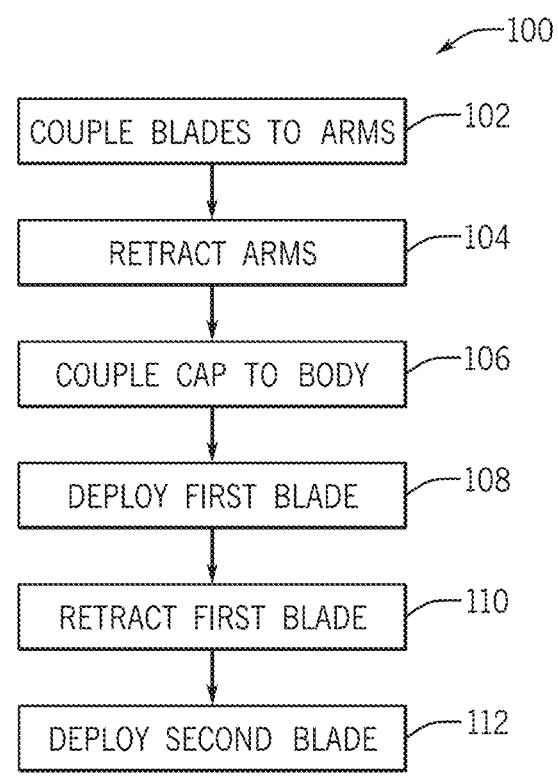
FIG. 8 is a flow chart of an embodiment of a method for using a handle system, in accordance with embodiments of the present disclosure.

FIG. 8 is a flow chart of an embodiment of a method 100 for using the handle system 10. It should be appreciated that the steps of the method 100 may be carried out in any order, in parallel, or with intervening steps unless otherwise specifically stated. In the illustrated embodiment, the blades 50 are coupled to the arms 80 (block 102). For example, the blades 50 may be particularly selected for anticipated upcoming uses and the tongue 52 and aperture 54 coupling system may be utilized to attach the blades 50 to the arms 80. It should be appreciated that the arms 80 may be rigidly coupled to the friction locker 82, and as a result the body 12, in various embodiments. Next, the arms 80 may be retracted into the respective slots 18 (block 104). Retracting the arms 80 may also retract the blades 50. By positioning the blades 50 within the slots 18, the likelihood that a user may engage the blades 50 inadvertently may be reduced. Furthermore, in various embodiments, the cap 34 may be coupled to the body 12 (block 106). Coupling the cap 34 to the body 12 may further protect against inadvertent engagement of the blades 50.

In various embodiments, one or more of the blades 50 may be deployed, for example during a surgical operation (block 108). Deployment of the blade 50 may include rotation in the first rotational direction 58 about the axis 28 to move the blade from the retracted position to the extended position. In various embodiments, the blade 50 may be in the extended position when it engages a lock or the rotation limiter 24, thereby securing the blade 50 in the extended position. However, it should be appreciated that, in various embodiments, locking or other engagement may not be a condition precedent for the blade 50 being in the extended position. Thereafter, the blade 50 may be retracted into to the slot 18 (block 110). In various embodiments, retraction of the blade 50 may include rotation in the second rotational direction 60 about the axis 28 to move the blade from the extended position to the retracted position. In various embodiments, the blade 50 may be in the retracted position when it engages a lock or a portion of the slot 18, thereby shrouding the blade 50 in the slot 18. However, it should be appreciated that, in various embodiments, locking or otherwise shrouding the blade 50 may not be a condition precedent for the blade 50 being in the retracted position. Next, a second blade 50 may be deployed (block 112). This second blade 50 may be on the same end as the first blade 50 or on a different end. In this manner, multiple blades 50 may be extended and retracted for use during a procedure while using the handle system 10.

The foregoing disclosure and description of the disclosed embodiments is illustrative and explanatory of the embodiments of the invention. Various changes in the details of the illustrated embodiments can be made within the scope of the appended claims without departing from the true spirit of the disclosure. The embodiments of the present disclosure should only be limited by the following claims and their legal equivalents.

The invention claimed is:

1. A multiple blade handle system, comprising:
   a body extending between a first end and a second end thereof;
   a first slot extending, at least partially, in the body, the first slot forming a cavity, the first slot arranged at the first end;
   a first carrier arranged, at least partially, within the first slot at the first end, the first carrier further comprising a friction locker and at least one first arm coupled to the friction locker, the at least one first arm being rotatable about the friction locker;
   a cap arranged on at least one of the first end and the second end;
   a first blade coupled to the at least one first arm, the first blade being rotatable about a first axis between a first retracted position where the first blade is positioned within the first slot and a first extended position where the first blade extends outwardly from the body;
   a second carrier arranged, at least partially, within a second slot positioned at the second end; and
   a second blade coupled to at least one second arm of the second carrier, the second blade being rotatable about a second axis between a second retracted position where the second blade is positioned within the second slot and a second extended position where the second blade extends outwardly from the body.

2. The multiple blade handle system of claim 1, wherein the body further comprises:
   an extendable body portion, the extendable body portion increasing a length of the body by adjusting the position of the extendable body portion relative to a first body portion of the body by means of a sliding mechanism of the multiple blade handle system.

3. The multiple blade handle system of claim 1, wherein the first blade and the second blade are independently rotatable.

4. The multiple blade handle system of claim 1, further comprising:
   a third arm coupled to the first carrier; and
   a third blade coupled to the third arm, the third blade being rotatable about the first axis between a third retracted position where the third blade is positioned within the first slot and a third extended position where the third blade extends outwardly from the body.

5. The multiple blade handle system of claim 4, wherein the second blade and the third blade are independently rotatable.

6. The multiple blade handle system of claim 4, wherein the first blade is a different size than the third blade.

7. The multiple blade handle system of claim 1, further comprising:
   a rotation limiter associated with the friction locker, wherein the rotation limiter restricts rotation of the first blade about the first axis.

8. The multiple blade handle system of claim 1, wherein the at least one first arm includes a tongue and the first blade includes a groove, the groove receiving the tongue to couple the first blade to the at least one first arm.

9. A multiple blade handle system, comprising:
   a body;
   a cavity formed within the body;
   a first carrier, having a plurality of arms, movable within the cavity, the plurality of arms being rotatable about a first axis of first carrier;
   a rotation limiter positioned proximate the plurality of arms and arranged within the cavity, the rotation limiter blocking rotation of the plurality of arms beyond a predetermined position;
   a first blade coupled to a first arm of the plurality of arms;
   a second blade coupled to a second arm of the plurality of arms;
   a second carrier, having a third arm, the third arm being rotatable about a second axis of the second carrier; and
   a third blade coupled to the third arm, the third arm rotatable about the second axis;
   wherein rotation of the first arm and the second arm is independent of rotation of the third arm.

10. The multiple blade handle system of claim 9, further comprising:
    a friction locker associated with the first carrier and arranged coaxially with the first axis, the friction locker restricting rotation of the first arm, about the first axis, when a rotational force is less than a set amount and enabling rotation of the first arm, about the first axis, when the rotational force is greater than the set amount.

11. The multiple blade handle system of claim 9, further comprising:
    a cap covering at least a portion of the cavity, the cap being coupled to the body.

12. The multiple blade handle system of claim 9, further comprising:
    a textured region along at least a portion of the body.

13. The multiple blade handle system of claim 9, wherein rotation of each of the first arm and the second arm is independent of one another.

14. The multiple blade handle system of claim 13, wherein the first blade is a different size than the second blade.

15. The multiple blade handle system of claim 9, further comprising:
    an extending body portion of the body, the extending body portion being axially translatable away with respect to a first body portion of the body via a sliding mechanism such that a length of the body is adjustable.

* * * * *